United States Patent [19]

Guskey et al.

[11] Patent Number: 6,123,932

[45] Date of Patent: Sep. 26, 2000

[54] DEODORANT COMPOSITIONS CONTAINING CYCLODEXTRIN ODOR CONTROLLING AGENTS

[75] Inventors: Gerald John Guskey, Montgomery; Dennis Ray Bacon, Milford; Prem Sagar Juneja, Cincinnati; Curtis Bobby Motley, West Chester; George Peter Rizzi, Cincinnati, all of Ohio

[73] Assignee: The Procter & Gamble Company, Cincinnati, Ohio

[21] Appl. No.: 09/332,215

[22] Filed: Jun. 14, 1999

[51] Int. Cl.[7] ............................... A61K 7/32; A61K 7/00; A61K 31/74; A61L 9/00
[52] U.S. Cl. ................................. 424/65; 422/5; 424/67; 424/78.03; 424/400; 424/401; 424/405
[58] Field of Search ..................... 424/65, 67, 69, 424/76.1, 76.2, 76.21, 76.4, 76.8, 78.03, 405, 642, 715, 717, 400, 401; 422/5

[56] References Cited

U.S. PATENT DOCUMENTS

| | | | |
|---|---|---|---|
| 4,803,195 | 2/1989 | Holzner | 512/4 |
| 5,135,747 | 8/1992 | Faryniarz et al. | 424/401 |
| 5,176,903 | 1/1993 | Goldberg et al. | 424/66 |
| 5,635,166 | 6/1997 | Galleguillos et al. | 424/66 |
| 5,672,340 | 9/1997 | Sun et al. | 424/66 |
| 5,861,144 | 1/1999 | Peterson et al. | 424/65 |
| 5,871,718 | 2/1999 | Lucas et al. | 424/65 |
| 5,874,070 | 2/1999 | Trinh et al. | 424/65 |
| 5,897,854 | 4/1999 | Lucas et al. | 424/65 |
| 5,942,214 | 8/1999 | Lucas et al. | 424/65 |

FOREIGN PATENT DOCUMENTS

| | | |
|---|---|---|
| 53-41440 | 4/1978 | Japan . |
| 3-284616 | 12/1991 | Japan . |
| 9-315937 | 12/1997 | Japan . |
| 10-120541 | 5/1998 | Japan . |
| WO 98/18439 | 5/1998 | WIPO . |

OTHER PUBLICATIONS

"Cyclodextrins in Foods, Cosmetics, and Toiletries." Hitoshi Hashimoto, 1996; (pp. 483–502).

*Primary Examiner*—Shelley A. Dodson
*Attorney, Agent, or Firm*—Joan B. Tucker; William J. Winter

[57] ABSTRACT

Disclosed are aqueous and anhydrous deodorant compositions which comprise from about 0.1% to about 89.9% by weight of a cyclodextrin odor controlling agent, from about 0.1% to about 30% by weight of a solid non-polymeric gellant and from about 10% to about 90% by weight of an aqueous or anhydrous liquid carrier. Also disclosed are methods of using and making the compositions. The disclosed compositions are especially effective at preventing or eliminating malodors resulting from perspiration.

21 Claims, No Drawings

DEODORANT COMPOSITIONS CONTAINING CYCLODEXTRIN ODOR CONTROLLING AGENTS

FIELD OF INVENTION

The present invention relates to aqueous and anhydrous deodorant compositions which are effective at preventing or eliminating malodors resulting from perspiration. In particular, the present invention relates to aqueous and anhydrous deodorant compositions which contain cyclodextrins that are especially effective at controlling malodors associated with human perspiration.

BACKGROUND OF THE INVENTION

Deodorant compositions are well known for use in controlling malodors associated with human perspiration. These malodors develop from human perspiration primarily as the result of microbial interaction with sweat gland secretions which then produces pungent fatty acids. Deodorant compositions typically contain deodorant actives such as antimicrobial agents to help control the microbial development of such malodors, and/or they can contain deodorizing fragrances that help to mask the sensory perception of the malodors.

Most deodorant compositions which contain antimicrobial agents and/or fragrances to control or mask malodors resulting from perspiration are typically formulated as deodorant sticks which also contain a gellant or other structurant, and a polar alcohol solvent to help solubilize the gellant or other structurant. These deodorant formulations are typically applied topically to the underarm or other area of the skin, and in addition to being effective at controlling or masking perspiration malodors these deodorant sticks can provide acceptable aesthetics such as clarity, ease of application, cool and refreshing feel on application, lack of powdery residue, and dry feel. Although these deodorant sticks are quite poplar and commonly used to control or mask malodors associated with human perspiration, many of these alcohol-containing deodorant sticks are also harsh to the skin and can cause excessive skin irritation after topical application.

Other attempts at controlling malodors resulting from perspiration include the use of odor absorbers such as activated charcoal and zeolites. Deodorant compositions which contain these perspiration malodor absorbing agents are typically formulated as aqueous lotions, aqueous roll-ons, and aqueous soft deodorant gels which comprise the odor absorber, and an aqueous liquid carrier. These activated charcoal and zeolite odor absorbing agents, however, can be ineffective when wet and are known to be inefficient at absorbing odors when they are included in aqueous systems, especially when the aqueous compositions are applied to the skin and the activated charcoal or zeolite comes in contact with human body fluids such as sweat.

Another attempt at controlling malodors resulting from perspiration include the use of cyclodextrin odor controlling agents. The use of cyclodextrins to absorb odors including body odors such as perspiration malodors, is well known. Deodorant compositions which contain cyclodextrin perspiration malodor controlling agents are also typically formulated as aqueous lotions, aqueous roll-ons, and aqueous soft deodorant gels. The aqueous soft deodorant gels are also referred to as deodorant creams. A typical example of such a cream deodorant formulation includes an alcohol-containing cream which comprise the cyclodextrin, an inorganic or polymeric gellant or thickening agent, and a polar alcohol solvent to help solubilize the gellant or thickening agent. These cyclodextrin-containing deodorant creams tend to be mild to the skin, and can be effective at preventing or eliminating perspiration malodors. Many consumers, however, still prefer the convenience of using a solid deodorant stick that is mild to the skin, and that is extremely effective at controlling perspiration malodors.

It has now been found that aqueous solid deodorant sticks can be formulated to contain cyclodextrin odor controlling agents which are extremely safe and mild to the skin, and which provide exceptional perspiration malodor controlling benefits. These new aqueous solid deodorant stick compositions comprise cyclodextrin that is highly effective in absorbing perspiration malodors, and that provides for improved perspiration malodor control without resulting in skin irritation after the compositions have been topically applied to the skin.

It has also been found that anhydrous deodorant compositions which are useful for preventing or eliminating malodors associated with perspiration can also be formulated to contain cyclodextrin odor controlling agents which are extremely safe and mild to the skin. Like the new aqueous solid deodorant sticks described above, these anhydrous deodorants provide for improved perspiration malodor control while also being non-irritating to the skin. These anhydrous deodorants, however, can be formulated as soft deodorant gels or sticks and preferably comprise non-polymeric gelling agents.

It is therefore an object of the present invention to provide an aqueous solid deodorant stick composition which provides improved perspiration malodor control, and which is extremely safe and mild to the skin. It is also an object of the present invention to provide an aqueous solid deodorant stick composition which contain cyclodextrin odor controlling agents to provide highly effective perspiration malodor absorbing benefits. It is yet another object of the present invention to provide anhydrous soft deodorant gel or stick compositions which are mild and non-irritating to the skin, and which contain cyclodextrin odor controlling agents which provide improved perspiration malodor controlling benefits.

SUMMARY OF THE INVENTION

The present invention is directed to aqueous deodorant compositions which comprise (a) from about 0.1% to about 89.9% by weight of a cyclodextrin; (b) from about 0.1% to about 30% by weight of a solid non-polymeric gellant that is substantially free of inorganic gelling agents; and (c) from about 10% to about 75% by weight of water; wherein the composition has a product hardness of less than about 200 pens.

The present invention is also directed to anhydrous deodorant compositions which comprise (a) from about 0.1% to about 89.9% by weight of a cyclodextrin; (b) from about 0.1% to about 30% by weight of a solid non-polymeric gellant; and (c) from about 10% to about 90% by weight of a non-aqueous liquid carrier.

It has been found that aqueous and anhydrous deodorant compositions, particularly aqueous deodorant sticks and anhydrous soft deodorant gels or sticks, can be formulated with cyclodextrin malodor controlling agents to provide improved malodor control that results from perspiration. These compositions are extremely mild to the skin, and causes little or no skin irritation while also being especially effective at preventing or eliminating perspiration malodors.

DETAILED DESCRIPTION OF THE INVENTION

The deodorant compositions of the present invention include aqueous and anhydrous deodorant formulations which are intended for topical application to the underarm or other suitable areas of the skin. These deodorant formulations comprise cyclodextrin which provides malodor controlling benefits, especially perspiration malodor controlling benefits.

The term "anhydrous" as used herein means that the deodorant composition of the present invention, and the essential or optional components thereof, are substantially free of added or free water. From a formulation standpoint, this means that the deodorant compositions of the present invention contain less than about 2%, preferably less than about 1%, more preferably less than about 0.5%, most preferably zero percent, by weight of free or added water.

The term "ambient conditions" as used herein refers to surrounding conditions at about one atmosphere of pressure, at about 50% relative humidity, at about 25° C.

The term "cyclodextrin" (CD) as used herein includes any of the known cyclodextrins such as unsubstituted cyclodextrins containing from six to twelve glucose units, especially alpha-cyclodextrin, beta-cyclodextrin, gamma-cyclodextrin, delta-cyclodextrin, epsilon-cyclodextrin, zeta-cyclodextrin, nu-cyclodextrin, and mixtures thereof, and/or their derivatives, and/or mixtures thereof.

The term "volatile" as used herein refers to those materials which have a measurable vapor pressure as measured at 25° C. Such vapor pressures will typically range from 0.01 mmHg to about 6 mmHg, more typically from about 0.02 mmHg to about 1.5 mmHg, and have an average boiling point at about 1 atm which is typically less than about 250° C., more typically less than about 235° C., at 1 atmosphere (atm) of pressure. Conversely, the term "non-volatile" refers to those materials which do not have a measurable vapor pressure or which have a vapor pressure of less than 0.01 mmHg as measured at 25° C., at 1 atm of pressure.

The solubility parameters for various solvents or other materials described herein are determined by methods well known in the chemical arts. A description of solubility parameters and means for determining them are described by C. D. Vaughan, "Solubility: Effects in Product, Package, Penetration and Preservation" 103 Cosmetics and Toiletries 47–69, October 1988; and C. D. Vaughan, "Using Solubility Parameters in Cosmetics Formulation", 36, J. Soc. Cosmetic Chemists 319–333, September/October, 1985; which descriptions are incorporated herein by reference.

The deodorant compositions of the present invention can comprise, consist of, or consist essentially of the essential elements and limitations of the present invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Cyclodextrins

The deodorant compositions of the present invention comprise cyclodextrin malodor controlling agents. The cyclodextrin can be used individually or as a mixture of cyclodextrins, provided that the cyclodextrin is capable of preventing or eliminating malodors associated with perspiration.

The cyclodextrins for use in the deodorant compositions of the present invention include those cyclic polysaccharide compounds containing from 6 to 12 glucose units. The specific coupling and conformation of the glucose units enable the cyclodextrin to form a rigid, conical molecular structure that has a hollow interior or cavity.

The cyclodextrins suitable for use herein are preferably included in the deodorant compositions of the present invention as an uncomplexed cyclodextrin. The term "uncomplexed cyclodextrin" as used herein means that the cavities within the cyclodextrin are essentially unfilled while the cyclodextrin is added into the liquid carrier component of the compositions of the present invention.

As will be apparent to those skilled in the art, the preferred uncomplexed cyclodextrin can form inclusion complexes with the other essential and/or optional components described herein. Therefore, it is preferred that at least an effective amount of the cyclodextrin be included in the deodorant compositions herein as an uncomplexed cyclodextrin, and should remain as an uncomplexed cyclodextrin until the compositions have been applied to the skin. In this context, the term "effective amount" means an amount of the cyclodextrin that is in its uncomplexed form when the cyclodextrin is added into the liquid carrier component described herein, and that remains uncomplexed until the cyclodextrin comes in contact with human body fluid such a sweat after the compositions have been topically applied to the skin.

The concentration of the cyclodextrin may vary with each selected deodorant formulation. Generally, the deodorant compositions of the present invention comprise the cyclodextrin at concentrations ranging from about 0.1% to about 89.9%, preferably from about 0.1% to about 50%, more preferably from about 0.1% to about 20%, most preferably from about 0.1% to about 10%, by weight of the composition.

Cyclodextrins for use herein include any of the known cyclodextrins such as unsubstituted cyclodextrins containing from 6 to 12 glucose units. Specific nonlimiting examples of such cyclodextrins include alpha-cyclodextrin, beta-cyclodextrin, gamma-cyclodextrin, delta-cyclodextrin, epsilon-cyclodextrin, zeta-cyclodextrin, nu-cyclodextrin, and mixtures thereof, and/or their derivatives, and/or mixtures thereof.

Suitable cyclodextrin derivatives include those cyclodextrin compounds of different degrees of substitution, specific examples of which include methyl-alpha-cyclodextrin, methyl-beta-cyclodextrin, hydroxyethyl-beta-cyclodextrin, hydroxypropyl-alpha-cyclodextrin, hydroxypropyl-beta-cyclodextrin, cyclodextrin glycerol ethers, maltose-bonded cyclodextrins, cationic cyclodextrins, quaternary ammonium cyclodextrins, anionic cyclodextrins such as carboxymethyl cyclodextrins, cyclodextrin sulfobutylethers, cyclodextrin sulfates, cyclodextrin succinylates, amphoteric cyclodextrins such as carboxymethyl/quaternary ammonium cyclodextrins, mono-3-6-anhydrocyclodextrins, and combinations thereof. Other examples of suitable cyclodextrin derivatives are disclosed in "Optimal Performances with Minimal Chemical Modification of Cyclodextrins", F. Diedaini-Pilard and B. Perly, The 7th International Cyclodextrin Symposium Abstracts, April 1994, p. 49; U.S. Pat. No. 3,426,011, issued to Parmerter et al. on Feb. 4, 1969; U.S. Pat. Nos. 3,453,257, 3,453,258, 3,453,259, and 3,453,260, all issued to Parmerter et al. on Jul. 1, 1969; U.S. Pat. No. 3,459,731, issued to Gramera et al. on Aug. 5, 1969; U.S. Pat. No. 3,553,191, issued to Parmerter et al. on Jan. 5, 1971; U.S. Pat. No. 3,565,887, issued to Parmerter et al. on Feb. 23, 1971; U.S. Pat. No. 4,535,152, issued to Szejtli et al. on Aug. 13, 1985; U.S. Pat. No. 4,616,008, issued to Hirai et al. on Oct. 7, 1986; U.S. Pat. No. 4,638,058, issued to Brandt et al. on Jan. 20, 1987; U.S. Pat. No. 4,746,734, issued to Tsuchiyama et al. on May 24, 1988; and U.S. Pat. No. 4,678,598, issued to Ogino et al. on Jul. 7, 1987; all of which disclosures are incorporated by reference herein.

Other suitable cyclodextrin materials for use herein include those individual cyclodextrins linked together, e.g., using multifunctional agents, to form oligomers, or other polymers. Nonlimiting examples of such materials include cyclodextrin polymers that are formed by crosslinking a cyclodextrin monomer with an aromatic, aliphatic, or cycloaliphatic polyfunctional crosslinking agent. Suitable cyclodextrin monomer materials include, but are not limited to, alpha-cyclodextrin, beta-cyclodextrin, gamma-cyclodextrin, delta-cyclodextrin, epsilon-cyclodextrin, zeta-cyclodextrin, nu-cyclodextrin, substituted alpha-cyclodextrin, substituted beta-cyclodextrin, and substituted gamma-cyclodextrin. Branched cyclodextrin monomer materials are also suitable for use herein. Specific examples of suitable polyfunctional crosslinking agents include, but are not limited to, diisocyanates, polyisocyanates, dihalohydrocarbons, and dihaloacetylhydrocarbons. Other suitable polyfunctional crosslinking agents can include asymmetric crosslinking agents containing different linking functionalities such as isocyanate, halo, or haloacetyl, an example of which include 4-isocyanatobenzoyl chloride. Specific examples of cyclodextrin polymers that are suitable for use herein include, but are not limited to, beta-cyclodextrin crosslinked by epichlorohydrin and ethyleneglycolbis (epoxypropyl ether); and alpha-, beta-, or gamma-cyclodextrin crosslinked by a polyisocyanate or dihalohydrocarbon polyfunctional crosslinking agent. Other polymeric forms are also suitable for use herein, such as carboxylic acid containing polymer-cyclodextrin conjugates which may be prepared by conjugating a suitable carboxylic acid containing polymer to a cyclodextrin monomer using any method well known in the art for preparing cyclodextrin polymers.

Preferred cyclodextrins suitable for use as a malodor controlling agent in the deodorant compositions of the present invention include alpha-cyclodextrin, beta-cyclodextrin, methyl-alpha-cyclodextrin, methyl-beta-cyclodextrin, hydroxypropyl-alpha-cyclodextrin, hydroxypropyl-beta-cyclodextrin. Beta-cyclodextrin, methyl-beta-cyclodextrin, and hydroxypropyl-beta-cyclodextrin are most preferred.

Alpha-cyclodextrin, beta-cyclodextrin, gamma-cyclodextrin and/or their derivatives can be obtained from, among others, Cerestar USA, Inc., located in Hammond, Ind.; Wacker Chemicals (USA), Inc., located in New Canaan, Conn.; Aldrich Chemical Company located in Milwaukee, Wis.; and Chinoin Pharmaceutical Works located in Budapest, Hungary.

It is also preferable to use a mixture of cyclodextrins. Such mixtures absorb perspiration malodors more broadly by complexing with odoriferous molecules that can vary widely in size. Mixtures of cyclodextrin can conveniently be obtained by using intermediate products from known processes for the preparation of cyclodextrins, examples of which include those processes described in U.S. Pat. No. 3,425,910 issued to Armbruster et al. on Nov. 29, 1983; and U.S. Pat. No. 4,738,923, issued to Ammeraal on Apr. 19, 1988; both descriptions of which are incorporated by reference herein. Preferably, at least a major portion of the cyclodextrin mixtures is alpha-cyclodextrin, beta-cyclodextrin, and/or gamma-cyclodextrin, more preferably beta-cyclodextrin. Some commercial examples of cyclodextrin mixtures are available from Ensuiko Sugar Refining Company located in Yokohama, Japan.

When the deodorant compositions of the present invention are formulated as an aqueous composition, the composition is preferably substantially free of hydroxyalkylated cyclodextrins such as hydroxyethyl-beta-cyclodextrin, hydroxypropyl-alpha-cyclodextrin, and hydroxypropyl-beta-cyclodextrin. In this context, the term "substantially free" means that the aqueous deodorant composition preferably contain less than an effective amount of such hydroxyalkylated cyclodextrins that when used alone would provide any malodor controlling benefits resulting from perspiration. Generally, the aqueous deodorant compositions of the present invention preferably contain less than 5%, more preferably less than 2%, even more preferably less than 1%, most preferably zero percent, of such hydroxyalkylated cyclodextrins by weight of the aqueous composition.

Gellant

The deodorant compositions of the present invention comprise a non-polymeric gellant suitable for providing the desired hardness and application characteristics to the compositions. The gellant concentrations typically range from about 0.1% to about 30%, preferably from about 0.1% to about 25%, more preferably from about 1% to about 20%, even more preferably from about 5% to about 20%, by weight of the deodorant compositions.

The aqueous deodorant compositions of the present invention comprise a solid non-polymeric gellant, other than inorganic gelling agents, that can melt and form a solution or other homogenous liquid or liquid dispersion with the liquid carrier as defined herein at a processing temperature of from about 50° C. to about 150° C., preferably from about 50° C. to about 120° C., more preferably from about 60° C. to about I 00C. Preferably, the aqueous deodorant compositions are substantially free of inorganic gelling agents. In this context, the term "substantially free" means that the aqueous deodorant compositions contain less than an effective amount of such gelling agents that when used alone would provide any thickening or measurable viscosity increase to the aqueous composition under ambient conditions. Generally, the aqueous deodorant compositions preferably contain less than 5%, more preferably less than 2%, even more preferably less than 1%, most preferably zero percent, of such inorganic gelling agents by weight of the aqueous composition. Examples of inorganic gelling agents to which the above-described negative limitations pertain include finely divided or colloidal silicas, fumed silicas, and silicates, which includes montmorillonite clays and hydrophobically treated montmorillonites, e.g., bentonites, hectorites and colloidal magnesium silicates.

Suitable gellants for use in the aqueous deodorant compositions of the present invention include, but are not limited to, fatty acid gellants, salts of fatty acids, hydroxy fatty acid gellants, esters and amides of fatty acid or hydroxy fatty acid gellants, cholesterolic materials, dibenzylidene alditols, lanolinolic materials, fatty alcohols, triglycerides, and other suitable solid non-polymeric gellants.

For anhydrous deodorant compositions of the present invention, any known non-polymeric gellant may be used provided that the selected non-polymeric gellant can melt and form a solution or other homogenous liquid or liquid dispersion with the liquid carrier as defined herein at a processing temperature as defined hereinabove. The selected non-polymeric gellant must also provide the deodorant composition with the desired gel matrix and product hardness after formulation and completion of processing.

Suitable non-polymeric gellants for use in the anhydrous deodorant compositions of the present invention include, but are not limited to, fatty acid gellants, salts of fatty acids, hydroxy fatty acid gellants, esters and amides of fatty acid or hydroxy fatty acid gellants, cholesterolic materials, dibenzylidene alditols, lanolinolic materials, fatty alcohols, triglycerides, inorganic materials such as clays or silicas, and other suitable non-polymeric gellants.

Preferred gellants for use in the aqueous and anhydrous deodorant compositions are the solid non-polymeric salts of fatty acids, wherein the fatty acid moiety has from about 12 to about 40 carbon atoms, preferably from about 12 to about 22 carbon atoms, more preferably from about 16 to about 20 carbon atoms, most preferably about 18 carbon atoms. Suitable salt forming cations for use with these gelling agents include metal salts such as alkali metals, e.g. sodium and potassium, and alkaline earth metals, e.g. magnesium, and aluminum. Preferred are sodium and potassium salts, more preferably sodium stearate, sodium palmitate, potassium stearate, potassium palmitate, sodium myristate, aluminum monostearate, and combinations thereof. Most preferred is sodium stearate. These gellants are preferably used at concentrations ranging from about 0.1% to about 30%, more preferably of from about 0.1% to about 25%, even more preferably from about 1% to about 20%, most preferably from about 5% to about 10%, by weight of the aqueous and anhydrous deodorant compositions.

Nonlimiting examples of other suitable solid non-polymeric gellants for use in the aqueous and anhydrous deodorant compositions include fatty alcohols having from about 8 to about 40 carbon atoms, preferably from 8 to about 30 carbon atoms, more preferably from about 12 to about 18 carbon atoms. These gellants are wax-like materials which are most typically used at concentrations ranging from about 1% to about 30%, preferably from about 5% to about 20%, most preferably from about 10% to about 20%, by weight of the aqueous and anhydrous deodorant compositions. Preferred are cetyl alcohol, myristyl alcohol, stearyl alcohol, behenyl alcohol, and combinations thereof, more preferably stearyl alcohol.

Nonlimiting examples of other suitable solid non-polymeric gellants for use in the aqueous and anhydrous deodorant compositions include fatty acid esters such as triglycerides. Specific examples of suitable triglyceride gelling agents include, but are not limited to, tristearin, tribehenin, behenyl palmityl behenyl triglyceride, palmityl stearyl palnityl triglyceride, hydrogenated vegetable oil, hydrogenated rape seed oil, castor wax, fish oils, tripalmitin, Syncrowax HRC and Syncrowax HGL-C (Syncrowax is available from Croda, Inc.). Other suitable glycerides include, but are not limited to, glyceryl stearate and glyceryl distearate. Preferred are glyceryl tribehenin and other triglycerides, wherein at least about 75%, preferably about 100%, of the esterified fatty acid moieties of said other triglycerides each have from about 18 to about 36 carbon atoms, and wherein the molar ratio of glyceryl tribehenin to said other triglycerides is from about 20:1 to about 1:1, preferably from about 10:1 to about 3:1, more preferably from about 6:1 to about 4:1. The esterified fatty acid moieties may be saturated or unsaturated, substituted or unsubstituted, linear or branched, but are preferably linear, saturated, unsubstituted ester moieties derived from fatty acid materials having from about 18 to about 36 carbon atoms. Most preferred is a triglyceride gelling agent comprising a combination of glyceryl tribehenin and C18–C36 triglyceride.

Nonlimiting examples of other suitable solid non-polymeric gellants for use in the aqueous and anhydrous deodorant compositions include fatty acids, and hydroxy fatty acids such as alpha or beta hydroxy fatty acids, having from about 10 to about 40 carbon atoms, and esters and amides of such gelling agents. Specific nonlimiting examples such gellants include 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof. Preferred are 12-hydroxystearic acid, esters of 12-hydroxystearic acid, amides of 12-hydroxystearic acid and combinations thereof, and all other solid non-polymeric gelling agents which correspond to the following formula:

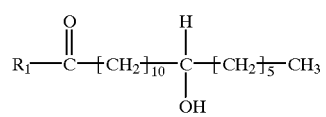

wherein $R_1$ is $OR_2$, $NR_2R_3$, or a silicone containing moiety; and $R_2$ and $R_3$ are hydrogen, or an alkyl, aryl, or arylalkyl radical which is branched linear or cyclic and has from about 1 to about 22 carbon atoms; preferably, from about 1 to about 18 carbon atoms. $R_2$ and $R_3$ may be either the same or different; however, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof; even more preferably, 12-hydroxystearic acid, isopropyl amide of 12-hydroxystearic acid, and combinations thereof. Most preferred is 12-hydroxystearic acid.

Nonlimiting examples of other suitable solid non-polymeric gellants for use in the aqueous and anhydrous deodorant compositions include disubstituted or branched monoamide gellants, monosubstituted or branched diamide gellants, triamide gellants, and combinations thereof, including n-acyl amino acid derivatives such as n-acyl amino acid amides, n-acyl amino acid esters prepared from glutamic acid, lysine, glutamine, aspartic acid, and combinations thereof. Other suitable amide gelling agents are described in U.S. Pat. No. 5,429,816 (Hofrichter et al.) and U.S. Pat. No. 5,840,287 (Guskey et al.), which descriptions are incorporated herein by reference. Concentrations of all such gellants preferably range from about 0.1% to about 25%, more preferably of from about 1% to about 15%, most preferably from about 5% to about 15%, by weight of the aqueous and anhydrous deodorant compositions.

Preferred Product Hardness

The deodorant compositions of the present invention are preferably in the form of a deodorant stick which has a product hardness of less than about 200 pens (measured in tenths of a millimeter), more preferably from about 50 pens to about 200 pens, most preferably from about 75 pens to about 120 pens.

The term "product hardness" as used herein is a reflection of how much force is required to move a penetration needle a specified distance and at a controlled rate into a deodorant composition under the following test conditions. Lower values represent harder product, and higher values represent softer product. These values can be determined according to the standard procedure set forth by ASTM Method D-5. The product hardness values used herein are measured using an automatic fixed time penetrometer (e.g., Fisher Scientific Co., Model 13-399-10 or equivalent), and a taper-tipped penetration needle as specified in ASTM Method-D 1321-DIN 51 579. The total weight of the needle and shaft in the penetrometer is 50.00±0.05 grams. The deodorant stick compositions are stored at about 26.7° C. (80° F.) for at least 24 hours prior to the determination of the product hardness values of the compositions.

Liquid Carrier

The deodorant compositions of the present invention comprise a liquid carrier suitable for topical application to human skin and appropriate for the product form desired. The liquid carrier is liquid under ambient conditions, and can include one or more liquid carrier materials provided that the any such combination of materials is in liquid form under ambient conditions.

Concentrations of the liquid carrier in the deodorant compositions will vary primarily with the type of product form desired, but for most product forms the concentration typically ranges from about 10% to about 90%, preferably from about 30% to about 75%, by weight of the deodorant composition.

Liquid carriers suitable for use in the deodorant compositions of the present invention include any topically safe and effective organic, silicone-containing or fluorine-containing, volatile or non-volatile, polar or non-polar liquid carrier, provided that the resulting combination of liquid carrier materials forms a solution or other homogenous liquid or liquid dispersion at the selected processing temperature of the composition. Processing temperatures for the deodorant compositions typically range from about 50° C. to about 150° C., more typically from about 50° C. to about 120° C., and even more typically from about 60° C. to about 100° C.

Nonlimiting examples of suitable liquid carriers include C1 to C20 monohydric alcohols, preferably C2 to C8 monohydric alcohols; C2 to C40 dihydric or polyhydric alcohols, preferably C2 to C20 dihydric or polyhydric alcohols; alkyl ethers of all such alcohols (preferably C1–C4 alkyl ethers); and polyalkoxylated glycols such as propylene glycols and polyethylene glycols having from 2 to 30 repeating alkoxylate (e.g., ethoxylate or propoxylate) groups; polyglycerols having from 2 to 16 repeating glycerol moieties; derivatives and combinations thereof.

Specific examples of such alcohol liquid carriers include propylene glycol; hexylene glycol; dipropylene glycol; tripropylene glycol; glycerin; propylene glycol methyl ether; dipropylene glycol methyl ether; ethanol; n-propanol; n-butanol; t-butanol; 2-methoxyethanol; 2-ethoxyethanol; ethylene glycol; isopropanol; isbutanol; 1,4-butylene glycol; 2,3-butylene glycol; trimethylene glycol; 1,3-butanediol; 1,4,-butanediol; propylene glycol monoisostearate; PPG-3 myristyl ether; PEG-4 (PEG-4 is also known as PEG-200); PEG-8 (PEG-8 is also known as PEG-400); 1,2, pentanediol; PPG-14 butylether; dimethyl isosorbide; and combinations thereof. Other similar but suitable solvents for use as liquid carriers are described, for example, in U.S. Pat. No. 4,781, 917 (Luebbe et al.), U.S. Pat. No. 5,643,558 (Provancal et al.), U.S. Pat. No. 4,816,261 (Luebbe et al.), EP 404 533 Al (Smith et al.), which descriptions are incorporated herein by reference.

Preferred liquid carriers include PPG-3 myristyl ether, propylene glycol, dipropylene glycol, tripropylene glycol, PEG-8, hexylene glycol, glycerin, and combinations thereof.

The deodorant compositions of the present invention preferably comprise a silicone liquid carrier in combination with an alcohol liquid carrier described hereinbefore. The concentration of the silicone liquid carrier preferably range from about 10% to about 90%, more preferably from about 15% to about 65%, by weight of the deodorant composition. The silicone liquid carriers suitable for use herein may be volatile or non-volatile silicones, provided that these silicone materials have the requisite volatility or non-volatility defined herein.

Nonlimiting examples of suitable silicone liquid carriers for use herein include those volatile silicones that are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 4 to about 6, silicon atoms. Most preferably are those which conform to the formula:

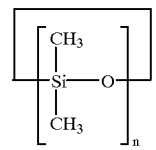

wherein n is from about 3 to about 7, preferably from about 4 to about 6, most preferably 5. These volatile cyclic silicones generally have a viscosity value of less than about 10 centistokes. All viscosity values described herein are measured or determined under ambient conditions, unless otherwise specified.

Other suitable silicone liquid carriers for use herein include those volatile and nonvolatile linear silicones which conform to the formula:

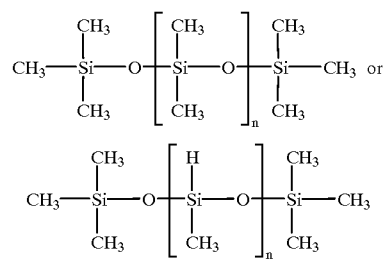

wherein n is greater than or equal to 0. The volatile linear silicone materials will generally have viscosity values of less than 5 cs at 25° C. The non-volatile linear silicone materials will generally have viscosity values of greater than 5 cs at 25° C.

Specific examples of suitable volatile silicones for use herein include, but are not limited to, hexamethyldisiloxane; Silicone Fluids SF-1202 and SF-1173 (commercially available from G. E. Silicones); Dow Corning 244, Dow Corning 245, Dow Corning 246, Dow Corning 344, and Dow Coming 345, (commercially available from Dow Coming Corp.); Silicone Fluids SWS-03314, SWS-03400, F-222, F-223, F-250, and F-251 (commercially available from SWS Silicones Corp.); Volatile Silicones 7158, 7207, 7349 (available from Union Carbide); Masil SF-V (available from Mazer); and combinations thereof.

Specific examples of suitable non-volatile linear silicones for use herein include, but are not limited to, Rhodorsil Oils 70047 available from Rhone-Poulenc; Masil SF Fluid available from Mazer; Dow Coming 200, and Dow Coming 225 (available from Dow Corning Corp.); Silicone Fluid SF-96 (available from G.E. Silicones); Velvasil and Viscasil (available from General Electric Co.); Silicone L-45, Silicone L-530, and Silicone L-531 (available from Union Carbide); and Siloxane F-221 and Silicone Fluid SWS-101 (available from SWS Silicones).

Other suitable non-volatile silicone liquid carriers for use in the deodorant compositions of the present invention include, but are not limited to, non-volatile silicone emollients such as polyalkylarylsiloxanes, polyestersiloxanes, polyethersiloxane copolymers, polyfluorosiloxanes, polyaminosiloxanes, and combinations thereof. These non-volatile silicone liquid carriers will generally have viscosity values of less than about 100,000 centistokes, preferably less than about 500 centistokes, more preferably from about 1 centistoke to about 200 centistokes, even more preferably from about 1 centistoke to about 50 centistokes, as measured under ambient conditions.

Other suitable liquid carriers for use in the deodorant compositions of the present invention include, but are not limited to, organic liquid carriers such as mineral oil, petrolatum, isohexadecane, isododecane, various other hydrocarbon oils, and combinations thereof. Preferred are mineral oil, and branched chain hydrocarbons having from about 4 to about 30 carbon atoms, preferably from about 4 to about 20 carbon atoms, more preferably from about 6 to about 20 carbon atoms. Specific non-limiting examples of suitable branched chain hydrocarbon oils include the isoparaffins available from Exxon Chemical Company, Baytown, Tex. U.S.A, as Isopar C (C7–C8 Isoparaffin), Isopar E (C8–C9 Isoparaffin), Isopar G (C10–11 Isoparaffin), Isopar H (C11–C12 Isoparaffin), Isopar L (C11–C13 Isoparaffm), Isopar M (C13–C14 Isoparaffin), and combinations thereof. Other nonlimiting examples of suitable branched chain hydrocarbons include Permethyl 99A (isododecane), Permethyl 102A (isoeicosane), Permethyl 101A (isohexadecane), and combinations thereof. The Permethyl series are available from Preperse, Inc., South Plainfield, N.J., U.S.A. Other non-limiting examples of suitable branched chain hydrocarbons include petroleum distillates such as those available from Phillips Chemical as Soltrol 130, Soltrol 170, and those available from Shell as Shell Sol 70, -71, and -2033, and combinations thereof.

Nonlimiting examples of other suitable organic liquid carriers include octyldodecanol, butyl stearate, diisopropyl adipate, dodecane, octane, decane and combinations thereof, and the Norpar series of paraffins available from Exxon Chemical Company as Norpar 12, -13, and -15. Yet another example includes C1–C15 alkanes/cycloalkanes available from Exxon as Exxsol D80. Yet another example includes the C12–C15 alkyl benzoates available as Finsolv-TN from Finetex located in Elmwood Park, N.J.

Other suitable liquid carriers include benzoate co-solvents, cinnamate esters, secondary alcohols, benzyl acetate, phenyl alkane, and combinations thereof.

The deodorant compositions of the present invention may be formulated as an aqueous or anhydrous composition. For an aqueous formulation, the deodorant compositions further comprise from about 10% to about 75% by weight of water, preferably from about 10% to about 60% by weight of water, more preferably from about 15% to about 50% by weight of water. For an anhydrous formulation, the deodorant compositions contain less than about 10%, more preferably less than about 3%, even more preferably less than about 1%, most preferably zero percent, by weight of water.

Optional Components

In addition to the essential components described hereinbefore, the deodorant compositions of the present invention may further comprise one or more optional components which may modify the physical or chemical characteristics of the compositions or serve as additional "active" components when deposited on the skin, provided that the optional components are physically and chemically compatible with the essential components described herein, or do not otherwise unduly impair product stability, aesthetics, or performance. Nonlimiting examples of such optional materials include components such as pH buffering agents; additional malodor controlling agents such as deodorant actives; fragrance materials; emollients; humectants; soothing agents; dyes and pigments; medicaments; baking soda and related materials; preservatives; and soothing agents such as aloe vera, allantoin, D-panthenol, avocado oil and other vegetative oils, and lichen extract. Some specific nonlimiting examples of preferred optional components are described in detail below.

Optional Deodorant Active

The deodorant compositions of the present invention may further comprise a deodorant active to help prevent or eliminate malodors resulting from perspiration. The concentration of the optional deodorant active ranges from about 0.001% to about 20%, preferably from about 0.01% to about 10%, more preferably from about 0.1% to about 5%, even more preferably from about 0.1% to about 1%, by weight of the composition. Suitable optional deodorant actives include any topical material, other than cyclodextrin, that is known or otherwise effective in preventing or eliminating malodor associated with perspiration. These deodorant actives are typically antimicrobial agents (e.g., bacteriocides, fungicides), malodor-absorbing material, or combinations thereof.

Preferred optional deodorant actives are antimicrobial agents, nonlimiting examples of which include cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

Optional Fragrance Materials

The deodorant compositions of the present invention may further comprise one or more fragrance materials to help cover or mask malodors resulting from perspiration, or which otherwise provide the compositions with the desired perfume aroma. These optional fragrances include any perfume or perfume chemical suitable for topical application to the skin.

The concentration of the optional fragrance in the deodorant compositions should be effective to provide the desired aroma characteristics or to mask malodor, wherein the malodor is inherently associated with the composition itself or is associated with malodor development from human perspiration. Also, the optional fragrance and whatever carriers accompany it should not impart excessive stinging to the skin, especially broken or irritated skin, at the concentrations disclosed herein. The optional fragrance can be include in the deodorant compositions of the present invention as free perfumes or as encapsulated perfume materials.

The optional free perfume for use in the deodorant compositions of the present invention include one or more individual perfume chemicals, provided that the optional free perfume can emit a detectable perfume odor or can mask or help to mask odors associated with perspiration. Generally, the deodorant compositions of the present invention comprise the optional free perfume at concentrations ranging from about 0.001% to about 20%, preferably from about 0.1% to about 10%, more preferably from about 0.5% to about 5%, by weight of the compositions.

In the event that the optional fragrance materials are included in the deodorant compositions as encapsulated perfume materials, the encapsulated perfume materials are preferably included as perfume/cyclodextrin complexes. The concentration of the optional perfume/cyclodextrin inclusion complex may vary with each selected deodorant formulation, but such concentrations will generally range from about 0.05% to about 20%, preferably from about 0.1% to about 10%, more preferably from about 2% to about 8%, by weight of the composition. Typically, the perfumes are included in the complex as a mixture of perfumes at a total perfume concentration ranging from about 0.1% to about 30%, preferably from about 1% to about 20%, more preferably from about 5% to about 15%, by weight of the complex.

Suitable cyclodextrin materials for use to form the optional perfume/cyclodextrin complexes include the cyclodextrins defined herein, nonlimiting specific examples of which include alpha-cyclodextrin, beta-cyclodextrin, gamma-cyclodextrin, delta-cyclodextrin, epsilon-cyclodextrin, zeta-cyclodextrin, nu-cyclodextrin, and mixtures thereof, and/or their derivatives, and/or mixtures thereof.

The optional perfume/cyclodextrin complexes can be formed in any of the ways known in the art or otherwise effective means of forming perfume/cyclodextrin inclusion complexes. Typically, the complexes are formed by mechanically mixing one molecule of perfume and one molecule of a cyclodextrin together in a suitable solvent such as water, or by kneading the molecules together in the presence of a suitable amount of solvent. However, the complexes can also be formed between one molecule of perfume and two molecules of cyclodextrin when the perfume material is large and contains two portions that can fit in the cyclodextrin. Preferably, the complexes are formed using mixtures of cyclodextrins since some perfumes are usually mixtures of materials that vary widely in size. It is preferred that at least a majority of the cyclodextrin mixture be alpha-, beta-, and/or gamma-cyclodextrin, more preferably beta-cyclodextrin.

Nonlimiting examples of fragrance materials suitable for use as an optional free perfume or an optional encapsulated perfume include any known fragrances in the art or any otherwise effective fragrance materials. Typical fragrances are described in Arctander, Perfume and Flavour Chemicals (Aroma Chemicals), Vol. I and II (1969); and Arctander, Perfume and Flavour Materials of Natural Origin (1960).

U.S. Pat. No. 4,322,308 and U.S. Pat. No. 4,304,679, both incorporated herein by reference, disclose fragrance components as generally including, but are not limited to, volatile phenolic substances (such as iso-amyl salicylate, benzyl salicylate, and thyme oil red); essence oils (such as geranium oil, patchouli oil, and petitgrain oil); citrus oils; extracts and resins (such as benzoin siam resinoid and opoponax resinoid); "synthetic" oils (such as Bergamot 37 and 430, Geranium 76 and Pomeransol 314); aldehydes and ketones (such as B-methyl naphthyl ketone, p-t-butyl-A-methyl hydrocinnamic aldehyde and p-t-amyl cyclohexanone); polycyclic compounds (such as coumarin and β-naphthyl methyl ether); esters (such as diethyl phthalate, phenylethyl phenylacetate, non-anolide-1:4).

Optional fragrances also include esters and essential oils derived from floral materials and fruits, citrus oils, absolutes, aldehydes, resinoides, musk and other animal notes (e.g., natural isolates of civet, castoreum and musk), balsamic, etc. and alcohols (such as dimyrcetol, phenylethyl alcohol and tetrahydromuguol). Specific nonlimiting examples of such components useful as optional fragrances herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, para-hydroxy phenolbutanone, 6-acetyl 1,1,3,4,4,6 hexamethyl tetrahydronaphthalene, alpha-methyl ionone, gamma-methyl ionone, amyl-cyclohexanone, and mixtures of these components.

Other suitable optional fragrances are those which mask or help to mask odors associated with perspiration (also referred to herein as odor masking fragrances), some nonlimiting examples of which are described in U.S. Pat. No. 5,554,588, U.S. Pat. No. 4,278,658, U.S. Pat. No. 5,501,805, and EP Patent Application 684 037 A1, all of which are incorporated herein by reference in their entirety. Preferred optional odor masking fragrances are those which have a Deodorant Value of at least about 0.25, more preferably from about 0.25 to about 3.5, even more preferably from about 0.9 to about 3.5, as measured by the Deodorant Value Test described in EP Patent Application 684 037 A1.

The optional fragrance for use herein may also contain solubilizers, diluents, or solvents which are well known in the art. Such materials are described in Arctander, Perfume and Flavour Chemicals (Aroma Chemicals), Vol. I and II (1969). These materials typically include small amounts of dipropylene glycol, diethylene glycol, $C_1$–$C_6$ alcohols, and/or benzyl alcohol.

Method of Manufacture

The deodorant compositions of the present invention may be prepared by any known or otherwise effective technique suitable for providing a deodorant composition having the essential materials described herein.

Methods for preparing the deodorant compositions of the present invention include conventional formulation and mixing techniques. Suitable methods include combining the cyclodextrin odor controlling agent with the liquid carrier. The gellant is then added with agitation and the solution is heated to a temperature of from about 75° C. to about 150C° to allow the gellant to melt. The resulting solution is cooled before adding fragrance (if applicable), and then the cooled composition is poured into an appropriate container or dispenser at about 70° C. and allowed to solidify within the container or dispenser by cooling or allowing to cool the contained composition to ambient temperature.

Method of Use

The deodorant compositions of the present invention may be topically applied to the axilla or other area of the skin in any known or otherwise effective method for controlling malodor associated with perspiration. These methods comprise applying to the axilla or other area of the human skin a safe and effective amount of the deodorant composition of the present invention. In this context, the term "safe and effective amount" means an amount of the deodorant composition topically applied to the skin which is effective in inhibiting or minimizing or masking perspiration malodor at the site of application while also being safe for human use at a reasonable risk/benefit ratio. In this context, a safe and effective amount typically ranges from about 0.1 gram per axilla to about 2.0 gram per axilla. The compositions are preferably applied to the axilla or other area of the skin one or more times daily, preferably once daily.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified concentrations are weight-weight percents, unless otherwise specified.

Examples I–VII

The following Examples I–VII describe aqueous deodorant stick compositions of the present invention. Each of the exemplified compositions are prepared by combining all of the listed components, except for the gellant and fragrance where applicable, and heating with agitation the combination of ingredients to a temperature above the melt point of the gellant but less than 150° C. The gellant is then added while continuing to heat and agitate the mixture until the gellant melts, at which point the liquid is cooled to a temperature of about 70° C. Fragrance is added with agitation to the cooled liquid. The fragrance-containing liquid is then poured into an appropriate dispenser or other container and allowed to solidify by cooling to ambient temperature.

Each of the exemplified aqueous deodorant stick compositions are applied topically to the underarm in an amount ranging from about 0.1 gram to about 2 grams per axilla. The compositions are effective in reducing, masking or eliminating perspiration odor, and are mild to the skin and cause little or no skin irritation.

| | Examples | | | | | | |
|---|---|---|---|---|---|---|---|
| Ingredient | I | II | III | IV | V | VI | VII |
| Beta-cyclodextrin | 5.00 | 10.00 | 5.00 | 5.00 | — | 2.50 | 1.00 |
| Alpha-cyclodextrin | — | — | — | — | — | — | 1.00 |
| Methy-beta-cyclodextrin | — | — | — | — | 5.00 | 2.50 | 1.00 |
| Butylene Glycol | — | 34.50 | — | — | — | — | — |
| Dipropylene Glycol | — | — | — | 44.43 | — | — | — |
| Hexylene Glycol | 38.50 | — | — | — | 20.00 | 20.00 | — |
| Propylene Glycol | — | — | — | 17.00 | — | — | 15.00 |
| Tetra Propylene Glycol | — | — | 40.43 | — | — | — | — |
| Ethanol | — | — | — | — | — | — | 58.20 |
| PEG 400 | 22.00 | 10.00 | 10.00 | — | 35.00 | 35.00 | — |
| Distilled H2O | 20.53 | 21.43 | 22.00 | 22.00 | 23.20 | 22.90 | 15.00 |
| Glycerin | 4.00 | 12.00 | 12.00 | — | 5.00 | 5.00 | — |
| PPG-3 Myristyl Ether | 1.70 | 1.70 | 1.00 | 1.50 | 1.13 | 1.14 | — |
| Sodium Hydroxide, 50% Soln. | 0.04 | 0.04 | 0.04 | 0.04 | 0.04 | 0.04 | — |
| Tetrasodium EDTA | 0.03 | 0.03 | 0.03 | 0.03 | 0.03 | 0.03 | — |
| Sodium Stearate | 5.20 | 5.50 | 5.50 | 5.50 | 5.60 | 5.60 | 5.00 |
| Triclosan | — | — | — | — | — | 0.30 | 0.30 |
| Fragrance | 3.00 | 4.00 | 2.50 | 3.00 | 3.50 | 3.50 | 2.00 |
| Color (PPG-3 M.E. solution) | — | 0.80 | 1.50 | 1.50 | 1.50 | 1.50 | 1.50 |

Examples VIII–XIII

The following Examples VIII–XIII describe anhydrous deodorant stick compositions of the present invention. Each of the exemplified compositions are prepared by combining all of the listed components, except for the gellant and fragrance where applicable, and heating with agitation the combination of ingredients to a temperature above the melt point of the gellant but less than 150° C. The gellant is then added while continuing to heat and agitate the mixture until the gellant melts, at which point the liquid is cooled to a temperature of about 70° C. Fragrance is added with agitation to the cooled liquid. The fragrance-containing liquid is then poured into an appropriate dispenser or other container and allowed to solidify by cooling to ambient temperature.

Each of the exemplified anhydrous deodorant stick compositions are applied topically to the underarm in an amount ranging from about 0.1 gram to about 2 grams per axilla. The compositions are effective in reducing, masking or eliminating perspiration odor, and are mild to the skin and cause little or no skin irritation.

| | Examples | | | | | |
|---|---|---|---|---|---|---|
| Ingredient | VIII | IX | X | XI | XII | XIII |
| Beta-cyclodextrin | — | — | 3.40 | 1.00 | — | — |
| Alpha-cyclodextrin | — | — | — | 1.00 | — | — |
| Methyl-beta-cyclodextrin | 10.00 | 10.00 | 3.40 | 1.00 | 0.30 | 6.00 |
| Sodium stearate | 3.20 | 3.70 | 3.90 | — | 3.50 | 3.50 |
| Triclosan | 0.30 | — | — | 0.10 | — | — |
| 12-hydroxystearic acid | — | — | — | 10.00 | — | — |
| Isopar V | 30.00 | — | — | — | 7.00 | 7.00 |
| Isopar M | 11.00 | — | 18.10 | 41.00 | 40.45 | 40.45 |
| Isopar L | — | — | 18.10 | — | — | — |
| Butyl stearate | 25.00 | 14.75 | 17.00 | 30.00 | — | — |
| Polydimethyl siloxane (50 cs) | — | 12.00 | 12.00 | — | — | — |
| PPG-3 myristyl ether | — | — | 0.60 | — | 3.50 | 3.50 |
| Mineral oil | — | — | — | — | 15.00 | 15.00 |
| 1,2-hexanediol | — | — | — | — | 12.75 | — |
| Hexylene glycol | 15.00 | 10.00 | 16.75 | — | — | 12.75 |
| Glycerin | 3.00 | 3.00 | 3.35 | — | 2.50 | 2.50 |
| Propylene glycol | — | — | — | 0.50 | — | — |
| Propylene glycol monoisostearate | — | — | — | — | 3.50 | — |
| Cyclopentasiloxane | — | — | — | 12.40 | — | — |
| Ethanol | — | — | — | — | 6.00 | 6.00 |
| Diisopropyl adipate | — | 18.00 | — | — | — | — |

-continued

| Ingredient | Examples | | | | | |
|---|---|---|---|---|---|---|
| | VIII | IX | X | XI | XII | XIII |
| Tripropylene glycol | — | 25.05 | — | — | — | — |
| Fragrance | 2.50 | 3.50 | 3.40 | 3.00 | 5.50 | 3.30 |

Examples XIV–XVI

The following Examples XIV–XVI describe anhydrous soft deodorant gel compositions of the present invention. Each of the exemplified compositions are prepared by combining all of the listed components, except for the gellant and fragrance where applicable, and heating with agitation the combination of ingredients to a temperature above the melt point of the gellant but less than 150° C. The gellant is then added while continuing to heat and agitate the mixture until the gellant melts, at which point the liquid is cooled to a temperature of about 55° C. Fragrance is added with agitation to the cooled liquid. The fragrance-containing liquid is then poured into an appropriate dispenser or other container and allowed to solidify by cooling to ambient temperature.

Each of the exemplified anhydrous soft deodorant gel compositions are applied topically to the underarm in an amount ranging from about 0.1 gram to about 2 grams per axilla. The compositions are effective in reducing, masking or eliminating perspiration odor, and are mild to the skin and cause little or no skin irritation.

| Ingredient | Examples | | |
|---|---|---|---|
| | XIV | XV | XVI |
| Beta-cyclodextrin | — | 3.00 | 5.00 |
| Alpha-cyclodextrin | — | 3.00 | 5.00 |
| Methyl-beta-cyclodextrin | 6.00 | — | 5.00 |
| Isopar M | 20.00 | — | 10.00 |
| Cyclopentasiloxane | 57.00 | 82.00 | 55.00 |
| Polydimethyl siloxane (50 cs) | 10.00 | 5.00 | 5.00 |
| Glyceryl tribehenin | 5.00 | 5.00 | — |
| C18–C36 triglycerides | 1.25 | 1.25 | — |
| Stearyl alcohol | — | — | 10.00 |
| Castor wax | — | — | 3.00 |
| Fragrance | 0.75 | 0.75 | 2.00 |

What is claimed is:

1. An aqueous deodorant composition comprising:
   (a) from about 0.1% to about 89.9% by weight of a cyclodextrin;
   (b) from about 0.1% to about 30% by weight of a solid non-polymeric gellant that is substantially free of inorganic gelling agents; and
   (c) from about 10% to about 75% by weight of water; wherein the composition has a product hardness of less than about 200 pens.

2. The composition of claim 1 wherein the composition has a product hardness of from about 75 pens to about 120 pens.

3. The composition of claim 2 wherein the composition comprises from about 0.1% to about 20% by weight of the cyclodextrin.

4. The composition of claim 3 wherein the cyclodextrin is selected from the group consisting of alpha-cyclodextrins, beta-cyclodextrins, gamma-cyclodextrins, delta-cyclodextrins, epsilon-cyclodextrins, zeta-cyclodextrins, nu-cyclodextrins, methyl-alpha-cyclodextrins, methyl-beta-cyclodextrins, hydroxyethyl-beta-cyclodextrins, hydroxypropyl-alpha-cyclodextrins, hydroxypropyl-beta-cyclodextrins, cyclodextrin glycerol ethers, maltose-bonded cyclodextrins, cationic cyclodextrins, quaternary ammonium cyclodextrins, anionic cyclodextrins, cyclodextrin sulfobutylethers, cyclodextrin sulfates, cyclodextrin succinylates, amphoteric cyclodextrins mono-3-6-anhydrocyclodextrins, and mixtures thereof.

5. The composition of claim 4 wherein the cyclodextrin is selected from the group consisting of alpha-cyclodextrins, beta-cyclodextrins, methyl-alpha-cyclodextrins, methyl-beta-cyclodextrins, hydroxypropyl-alpha-cyclodextrins, hydroxypropyl-beta-cyclodextrins, and mixtures thereof.

6. The composition of claim 2 wherein the solid non-polymeric gellant is selected from the group consisting of fatty acid gellants, salts of fatty acids, esters of fatty acids, amides of fatty acids, hydroxy fatty acids, cholesterolic materials, dibenzylidene alditols, lanolinolic materials, fatty alcohols, triglycerides, and mixtures thereof.

7. The composition of claim 6 wherein the solid non-polymeric gellant is a fatty acid salt selected from the group consisting of sodium stearate, sodium palmitate, potassium stearate, potassium palmitate, sodium myristate, aluminum monostearate, and mixtures thereof.

8. The composition of claim 1 wherein the composition further comprises a non-aqueous liquid carrier selected from the group consisting of propylene glycol monoisostearate, PPG-3 myristyl ether, PEG-4, PEG-8, 1,2, pentanediol, PPG-14 butyl ether, dimethyl isosorbide, propylene glycol, hexylene glycol, dipropylene glycol, tripropylene glycol, glycerin, propylene glycol methyl ether, dipropylene glycol methyl ether, ethanol, n-propanol, n-butanol, t-butanol, 2-methoxyethanol, 2-ethoxyethanol, ethylene glycol, isopropanol, isbutanol, 1,4-butylene glycol, 2,3-butylene glycol, trimethylene glycol, 1,3-butanediol, 1,4,-butanediol, volatile silicones, non-volatile silicones, butyl stearate, C12–C15 alkyl benzoates, mineral oil, petrolatum, octyldodecanol, diisopropyl adipate, isohexadecane, isododecane, isoparaffins and mixtures thereof.

9. The composition of claim 8 wherein the composition further comprises from about 0.001% to about 20% by weight of a deodorant active selected from the group consisting of cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides, zinc citrate, zinc salicylate, zinc pyrithione, zinc phenolsulfate, farnesol, and mixtures thereof.

10. The composition of claim 8 wherein the composition further comprises a fragrance material selected from the group consisting of free perfumes, cyclodextrin encapsulated perfumes, and mixtures thereof.

11. An anhydrous deodorant composition comprising:
   (a) from about 0.1% to about 89.9% by weight of a cyclodextrin;
   (b) from about 0.1% to about 30% by weight of a solid non-polymeric gellant; and
   (c) from about 10% to about 90% by weight of a non-aqueous liquid carrier.

12. The composition of claim 11 wherein the composition comprises from about 0.1% to about 20% by weight of the cyclodextrin.

13. The composition of claim 12 wherein the cyclodextrin is selected from the group consisting of alpha-cyclodextrins, beta-cyclodextrins, gamma-cyclodextrins, delta-cyclodextrins, epsilon-cyclodextrins, zeta-cyclodextrins, nu-cyclodextrins, methyl-alpha-cyclodextrins, methyl-beta-cyclodextrins, hydroxyethyl-beta-cyclodextrins, hydroxypropyl-alpha-cyclodextrins, hydroxypropyl-beta-cyclodextrins, cyclodextrin glycerol ethers, maltose-bonded cyclodextrins, cationic cyclodextrins, quaternary ammonium cyclodextrins, anionic cyclodextrins, cyclodextrin sulfobutylethers, cyclodextrin sulfates, cyclodextrin succinylates, amphoteric cyclodextrins mono-3-6-anhydrocyclodextrins, and mixtures thereof.

14. The composition of claim 13 wherein the cyclodextrin is selected from the group consisting of alpha-cyclodextrins, beta-cyclodextrins, methyl-alpha-cyclodextrins, methyl-beta-cyclodextrins, hydroxypropyl-alpha-cyclodextrins, hydroxypropyl-beta-cyclodextrins, and mixtures thereof.

15. The composition of claim 11 wherein the solid non-polymeric gellant is selected from the group consisting of fatty acid gellants, salts of fatty acids, esters of fatty acids, amides of fatty acids, hydroxy fatty acids, cholesterolic materials, dibenzylidene alditols, lanolinolic materials, fatty alcohols, triglycerides, clays, silicas, and mixtures thereof.

16. The composition of claim 15 wherein the solid non-polymeric gellant is a fatty acid salt selected from the group consisting of sodium stearate, sodium palmitate, potassium stearate, potassium palmitate, sodium myristate, aluminum monostearate, and mixtures thereof.

17. The composition of claim 11 wherein the non-aqueous liquid carrier is selected from the group consisting of propylene glycol monoisostearate, PPG-3 myristyl ether, PEG-4, PEG-8, 1,2, pentanediol, PPG-14 butylether, dimethyl isosorbide, propylene glycol, hexylene glycol, dipropylene glycol, tripropylene glycol, glycerin, propylene glycol methyl ether, dipropylene glycol methyl ether, ethanol, n-propanol, n-butanol, t-butanol, 2-methoxyethanol, 2-ethoxyethanol, ethylene glycol, isopropanol, isbutanol, 1,4-butylene glycol, 2,3-butylene glycol, trimethylene glycol, 1,3-butanediol, 1,4,-butanediol, volatile silicones, non-volatile silicones, butyl stearate, C12–C15 alkyl benzoates, mineral oil, petrolatum, octyldodecanol, diisopropyl adipate, isohexadecane, isododecane, isoparaffins and mixtures thereof.

18. The composition of claim 11 wherein the composition further comprises from about 0.001% to about 20% by weight of a deodorant active selected from the group consisting of cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides, zinc citrate, zinc salicylate, zinc pyrithione, zinc phenolsulfate, famesol, and mixtures thereof.

19. The composition of claim 11 wherein the composition further comprises a fragrance material selected from the group consisting of free perfumes, cyclodextrin encapsulated perfumes, and mixtures thereof.

20. A method for controlling malodor associated with human perspiration, which method comprises the step of applying to an underarm area of the skin the composition of claim 1.

21. A method for controlling malodor associated with human perspiration, which method comprises the step of applying to an underarm area of the skin the composition of claim 11.

* * * * *

UNITED STATES PATENT AND TRADEMARK OFFICE
CERTIFICATE OF CORRECTION

PATENT NO. : 6,123,932
DATED : September 26, 2000
INVENTOR(S) : Guskey et al.

It is certified that error appears in the above-identified patent and that said Letters Patent is hereby corrected as shown below:

Column 7,
Line 48, "palnityl" should read -- palmityl --.

Column 10,
Lines 61-62, "Coming 345" should read -- Corning 345 --.

Column 11,
Line 4, "Coming 200" should read -- Corning 200 --.
Line 4, "Coming 225" should read -- Corning 225 --.
Line 37, "Isoparaffm" should read -- Isoparaffin --.
Line 53, "C1-C15" should read -- C11-C15 --.

Column 18,
Line 39, "isoparaffms" should read -- isoparaffins --.
Line 53, "famesol" should read -- farnesol --.

Column 20,
Line 22, "famesol" should read -- farnesol --.

Signed and Sealed this

Second Day of December, 2003

JAMES E. ROGAN
*Director of the United States Patent and Trademark Office*